United States Patent
Miyake et al.

(10) Patent No.: US 10,221,123 B1
(45) Date of Patent: Mar. 5, 2019

(54) PROCESS FOR PREPARING (4Z,7Z)-4,7-DECADIEN-1-YL ACETATE

(71) Applicant: SHIN-ETSU CHEMICAL CO., LTD., Tokyo (JP)

(72) Inventors: Yuki Miyake, Joetsu (JP); Takeshi Kinsho, Joetsu (JP); Yusuke Nagae, Joetsu (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 0 days.

(21) Appl. No.: 16/048,943

(22) Filed: Jul. 30, 2018

(30) Foreign Application Priority Data

Sep. 7, 2017 (JP) .................................. 2017-172211

(51) Int. Cl.
| | | |
|---|---|---|
| *C07C 67/10* | (2006.01) | |
| *C07C 17/263* | (2006.01) | |
| *C07C 17/354* | (2006.01) | |

(52) U.S. Cl.
CPC .......... *C07C 67/10* (2013.01); *C07C 17/2632* (2013.01); *C07C 17/354* (2013.01)

(58) Field of Classification Search
CPC .... C07C 67/10; C07C 17/2631; C07C 17/354
USPC ....................................................... 560/236
See application file for complete search history.

(56) References Cited

FOREIGN PATENT DOCUMENTS

EP         0040829 A2     12/1981

OTHER PUBLICATIONS

Levi-Zada, Anat et. al., "Reevaluation of the Sex Pheromone of the Lesser Date Moth, *Batrachedra amydraula*, Using Autosampling SPME-GC/MS and Field Bioassays", (2013), Chemoecology, vol. 23: pp. 13-20.

Levi-Zada, Anat et. al., "Identification of the Sex Pheromone of the Lesser Date Moth, *Batrachedra amydraula*, Using Sequential SPME Auto-Sampling", (2011), Tetrahedron Letters, vol. 52: pp. 4550-4553.

Jan. 16, 2019 Search Report issued in European Patent Application No. 18191079.5.

Puigmarti, Marc et. al., "An Improved and Convenient New Synthesis of the Pheromone Components of the Tomato Leafminer Tuta Absoluta", Synthesis, vol. 47, No. 07, pp. 961-968, (Jan. 15, 2015).

Hungerford, Natasha L. et. al., "Titanium(II)-Based Z-Reduction of Alkynes. Syntheses of Deuterium Labelled Linolenic and Oleic Acids and (3E,8Z,11Z)-Tetradeca-3,8,11-Trienyl Acetate, the Sex Pheromone of a Tomato Pest, Scrobipalpuloides Absoluta", Journal of the Chemical Society, Perkin Transactions 1, No. 11, pp. 1839-1858, (Jan. 1, 1998).

*Primary Examiner* — Deborah D Carr
(74) *Attorney, Agent, or Firm* — Oliff PLC

(57) ABSTRACT

A high-yield process for preparing (4Z,7Z)-4,7-decadien-1-yl acetate, with reduced number of steps, without using a protecting group. A process for preparing (4Z,7Z)-4,7-decadien-1-yl acetate is provided, the process including at least the following steps: reducing a 10-halo-3,6-decadiyne of the general formula (1) to form a (3Z,6Z)-10-halo-3,6-decadiene of the general formula (2); and converting the (3Z,6Z)-10-halo-3,6-decadiene into (4Z,7Z)-4,7-decadien-1-yl acetate of the formula (4) having an acetoxy group in place of the halogen atom of the (3Z,6Z)-10-halo-3,6-decadiene.

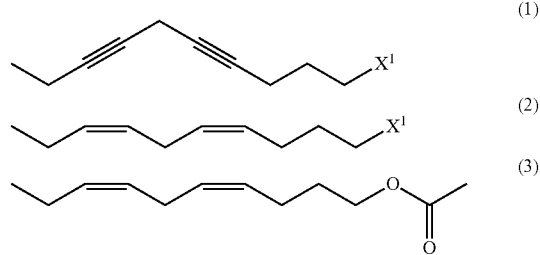

5 Claims, No Drawings

PROCESS FOR PREPARING (4Z,7Z)-4,7-DECADIEN-1-YL ACETATE

TECHNICAL FIELD

The present invention relates to a process for preparing (4Z,7Z)-4,7-decadien-1-yl acetate, which is a sex pheromone of the lesser date moth which is an insect pest serious for date palm.

BACKGROUND ART

Lesser date moth (*Batrachedra amydraula*) is one of the most serious pests that attack date palm in the Middle East and North Africa. As its larvae feed on fruits and soft immature seeds of date palm to make holes near the fruit calyx to enter the pulp, so that they damage the fruits. Infested fruit becomes dark in about four weeks after the attack, and fruit bunch stops growing. Thus, infested fruit turns into dry and falls to the ground, leading a decreased crop. It is difficult to control the pest by insecticides, because the larvae are inside the pulp. Therefore, biological pest control has been attracting great interest, and the use of a sex pheromone is expected for such biological control.

The sex pheromone of the lesser date moth was identified as a 2:2:1 mixture of (5Z)-5-decen-1-yl acetate, (5Z)-5-decen-1-ol and (4Z,7Z)-4,7-decadien-1-yl acetate (Non Patent Literature 1).

Anat Levi-Zada et al. reports a method for producing (4Z,7Z)-4,7-decadien-1-yl acetate, sex pheromone of the lesser date moth, in which 1-(tetrahydropyranyloxy)-4-pentyne is deprotonated, coupled with 2-pentynyl tosylate in the presence of a copper iodide dimethyl sulfide complex to form 1-(tetrahydropyranyloxy)-4,7-decadiyne, which is further converted, by hydroboration and subsequent protonation, into 1-(tetrahydropyranyloxy)-(4Z,7Z)-4,7-decadiene, which is then subjected to simultaneous deprotection and acetylation of the tetrahydropyranyl group (hereinafter referred to also as "THP group") (Non Patent Literature 2).

LIST OF PRIOR ART

Non Patent Literature

[Non Patent Literature 1] Anat Levi-Zada, et al., "Reevaluation of the sex pheromone of the lesser date moth, *Batrachedra amydraula*, using autosampling SPME-GC/MS and field bioassays", 2013, Chemoecology, 23: 13-20

[Non Patent Literature 2] Anat Levi-Zada et al., "Identification of the sex pheromone of the lesser date moth, *Batrachedra amydraula*, using sequential SPME autosampling", 2011, Tetrahedron Letters, 52: 4550-4553.

SUMMARY OF THE INVENTION

Problems to be Solved

However, the total yield based on 1-(tetrahydropyranyloxy)-4-pentyne is as low as 30% in the method described in Non Patent Literature 2. The method is not cost effective, as it requires Amberlyst-15, which is an expensive solid acid catalyst, in the step of deprotection and acetylation of THP group. Further, it requires removal of a large quantity of Amberlyst-15 by filtration, which makes it difficult to implement the method in a general manufacturing facility. In addition, the use of a protecting group such as a THP group requires two steps: a step of protecting a hydroxyl group and a step of its deprotection, increasing the total number of reaction steps, which is undesirable in industrial production. Further, because the deprotection of an ether type protecting group such as the THP group is an equilibrium reaction, a portion of the protecting group remains after the deprotection, which may lead to a decreased yield.

Means to Solve the Problems

Through extensive research, the present inventors have found that (4Z,7Z)-4,7-decadien-1-yl acetate can be prepared, in a good yield with the reduced number of steps, without using a protective group in any step, by a process comprising at least the steps of: reducing a 10-halo-3,6-decadiyne to form a (3Z,6Z)-10-halo-3,6-decadiene; and converting the (3Z,6Z)-10-halo-3,6-decadiene into (4Z,7Z)-4,7-decadien-1-yl acetate having an acetoxy group in place of the halogen atom of the (3Z,6Z)-10-halo-3,6-decadiene.

According to one aspect of the invention, a process for preparing (4Z,7Z)-4,7-decadien-1-yl acetate is provided. The process comprises at least the following steps:

reducing a 10-halo-3,6-decadiyne of the general formula (1):

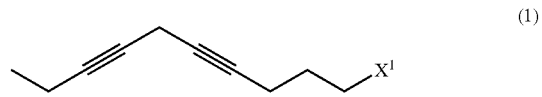

wherein $X^1$ is a halogen atom,
to form a (3Z,6Z)-10-halo-3,6-decadiene of the general formula (2):

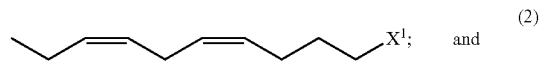

and converting the (3Z,6Z)-10-halo-3,6-decadiene into (4Z,7Z)-4,7-decadien-1-yl acetate of the formula (4) having an acetoxy group in place of the halogen atom of the (3Z,6Z)-10-halo-3,6-decadiene:

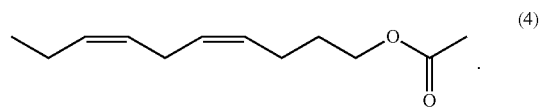

According to one preferable embodiment, a 10-halo-3,6-decadiyne of the general formula (1) is prepared by a process comprising steps of:

deprotonating a 5-halo-1-pentyne of the general formula (5):

wherein $X^1$ is a halogen atom,
by a reaction with a Grignard reagent of the general formula (6):

wherein R is a monovalent hydrocarbon group having 1-18 carbon atoms, and X² is a halogen atom,
to yield a 5-halo-1-pentynyl magnesium halide of the general formula (7):

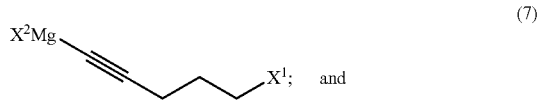
(7)

coupling the 5-halo-1-pentynyl magnesium halide, in the presence of a copper catalyst, with a 1-halo-2-pentyne of the general formula (8):

(8)

wherein X³ is a halogen atom,
to form a 10-halo-3,6-decadiyne of the general formula (1).

Advantageous Effects of the Invention

According to the present invention, (4Z,7Z)-4,7-decadien-1-yl acetate can be prepared in a high yield with the reduced number of steps, without using a protective group in any step.

DESCRIPTION OF EMBODIMENTS

In the present application, whenever compounds before and after a reaction have a substituent denoted by a same symbol, it is intended that they have the same substituent due to the nature of the reaction. For example, $X^1$ is a halogen atom in general. In a case where a chlorine atom is chosen for $X^1$ in formula (1), then $X^1$ in each of the formulae (2), (5) and (7) also is a chlorine atom. On the other hand, substituents denoted by different symbols such as $X^1$ and $X^2$ may be the same or different substituent groups.

First, the preparation of a 10-halo-3,6-decadiyne (1) will be described in more detail.

In a first step, a 5-halo-1-pentyne (5) is deprotonated by the reaction with a Grignard reagent (6) to form a 5-halo-1-pentynyl magnesium halide (7).

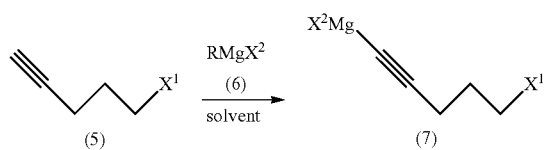

In the 5-halo-1-pentyne of the general formula (5), $X^1$ is a halogen atom, non-limiting examples of which include chlorine, bromine and iodine atoms, and is identical with $X^1$ in the formula (1) for the 10-halo-3,6-decadiyne.

Non-limiting examples of the 5-halo-1-pentyne include 5-chloro-1-pentyne, 5-bromo-1-pentyne, and 5-iodo-1-pentyne. In view of the reactivity and the yield of 10-halo-3,6-decadiyne (1), 5-chloro-1-pentyne and 5-bromo-1-pentyne are preferable, with 5-chloro-1-pentyne being more preferable.

A 5-halo-1-pentyne (5) is commercially available, or may be prepared by halogenation of a commercially available 4-pentyne-1-ol.

In the general formula (6) of the Grignard reagent, R is a monovalent hydrocarbon group having 1 to 18 carbon atoms, preferably 1 to 6 carbon atoms.

Non-limiting examples of the monovalent hydrocarbon group R include linear, saturated hydrocarbon groups, such as methyl, ethyl, n-propyl, n-butyl, n-pentyl, n-hexyl, n-heptyl, n-octyl, n-nonyl, n-decyl, n-undecyl, n-dodecyl, n-tridecyl, n-tetradecyl, n-pentadecyl, n-hexadecyl, n-heptadecyl and n-octadecyl groups; branched, saturated hydrocarbon groups, such as isopropyl, isobutyl and isopentyl groups; linear, unsaturated hydrocarbon groups, such as vinyl, 1-propenyl, 1-butenyl, 2-propenyl, 2-butenyl, 3-butenyl, 1-propynyl and 2-propynyl groups; branched, unsaturated hydrocarbon groups, such as isopropenyl and 2-methyl-2-propenyl groups; cyclic hydrocarbon groups, such as cyclopropyl, 2-methylcyclopropyl, cyclobutyl and cyclopentyl groups; and isomers thereof. Also, a part of the hydrogen atoms in these hydrocarbon groups may be substituted with, e.g., a methyl or ethyl group.

In the general formula (6), $X^2$ is a halogen atom, non-limiting examples of which include chlorine, bromine and iodine atoms.

Non-limiting examples of the Grignard reagent (6) include Grignard reagents having a linear hydrocarbon moiety, such as methyl magnesium chloride, ethyl magnesium chloride, n-propyl magnesium chloride, n-butyl magnesium chloride, methyl magnesium bromide, ethyl magnesium bromide, n-propyl magnesium bromide, n-butyl magnesium bromide, methyl magnesium iodide, ethyl magnesium iodide, n-propyl magnesium iodide, and n-butyl magnesium iodide; and Grignard reagents having a branched hydrocarbon moiety, such as isopropyl magnesium chloride, isopropyl magnesium bromide, and isopropyl magnesium iodide. In view of the suppression of dehalogenation side-reaction, Grignard reagents having a linear hydrocarbon moiety are preferred, such as methyl magnesium chloride, ethyl magnesium chloride, methyl magnesium bromide, ethyl magnesium bromide, methyl magnesium iodide, and ethyl magnesium iodide.

In view of the reactivity, the Grignard reagent (6) is used preferably in an amount of from 1.0 to 1.5 moles per mole of the 5-halo-1-pentyne (5).

A solvent may be used in the deprotonation. Examples of the solvent include hydrocarbon solvents, such as toluene, xylene, and hexane; and ether solvents, such as tetrahydrofuran, 4-methyltetrahydropyran, and diethyl ether. In view of the reactivity, tetrahydrofuran is preferable.

In view of the yield, the solvent is used preferably in an amount of from 100 to 1,500 grams per mole of the 5-halo-1-pentyne (5).

The temperature in the deprotonation is preferably in a range of from 40 to 70° C. in view of the reaction rate.

The duration of the deprotonation step may vary depending on a scale of a reaction system. It ranges preferably from 1 to 10 hours in view of the yield.

Non-limiting examples of $X^1$ in the 5-halo-1-pentynyl magnesium halide of the general formula (7) are as mentioned above.

Non-limiting examples of the 5-halo-1-pentynyl magnesium chloride (7) include 5-chloro-1-pentynyl magnesium chloride, 5-bromo-1-pentynyl magnesium chloride, 5-iodo-1-pentynyl magnesium chloride, 5-chloro-1-pentynyl magnesium bromide, 5-bromo-1-pentynyl magnesium bromide, 5-iodo-1-pentynyl magnesium bromide, 5-chloro-1-pentynyl magnesium iodide, 5-bromo-1-pentynyl magnesium iodide, and 5-iodo-1-pentynyl magnesium iodide.

For example, in a case where 5-chloro-1-pentyne (5A) is deprotonated to obtain a Grignard reagent (7A), wherein the suffix "A" indicates that $X^1$ is a chlorine atom, it may be expected that a cross-coupling between unreacted 5-chloro-1-pentyne (5A) and 5-chloro-1-pentynyl magnesium halide (7A), or a homocoupling of 5-chloro-1-pentynyl magnesium halide (7A) would occur. However, it has been found that these reactions proceed hardly due to low elimination capability of the chlorine atom. This is considered to contribute to the high yield of 10-chloro-3,6-decadiyne (1A).

In the next step, the 5-halo-1-pentynyl magnesium halide (7) is coupled with a 1-halo-2-pentyne (8) in the presence of a copper catalyst to prepare a 10-halo-3,6-decadiyne (1).

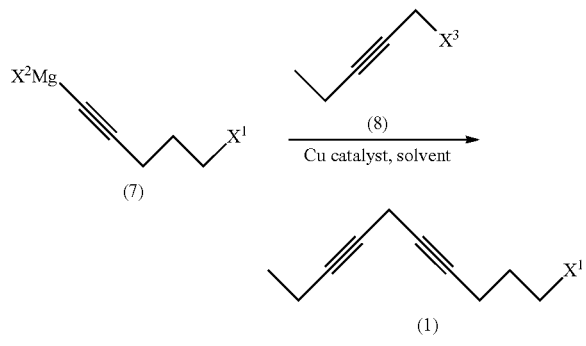

In the 1-halo-2-pentyne of the general formula (8), $X^3$ is a halogen atom, non-limiting examples of which include chlorine, bromine and iodine atoms.

Non-limiting examples of the 1-halo-2-pentyne (B) include 1-chloro-2-pentyne, 1-bromo-2-pentyne, and 1-iodo-2-pentyne. In view of the reactivity, 1-bromo-2-pentyne and 1-iodo-2-pentyne are preferable, with 1-bromo-2-pentyne being more preferable.

In view of the suppression of side reactions, the amount of the 1-halo-2-pentyne (8) to be used in the coupling reaction is preferably in a range of from 0.90 to 1.30 moles per mole of the 5-halo-1-pentyne (5).

Non-limiting examples of the copper catalyst that may be used in the coupling reaction include cuprous halides, such as cuprous chloride, cuprous bromide, and cuprous iodide; and cupric halides, such as cupric chloride, cupric bromide, and cupric iodide. In view of the reactivity, cuprous halides are preferable, with cuprous chloride being more preferable.

In view of the reaction rate and post-processing, the amount of the copper catalyst to be used in the coupling reaction is preferably in a range of from 0.003 to 0.300 mole per mole of the 5-halo-1-pentyne (5).

Types and amounts of the solvent that may be used in the coupling reaction are as described for the solvents that may be used in the deprotonation.

The coupling reaction may be carried out in situ after the deprotonation, or in a different reaction system.

A coupling reaction at the propargyl position may involve competition between the $S_N2$ and $S_N2'$ reactions. The $S_N2'$ reaction gives by-products having an allene structure, leading to a decreased yield. Further, when a compound containing an oxygen atom which is prone to interact with copper or magnesium is used, steric bulkiness may increase around the reaction point due to interaction with the metal atom. In contrast, steric bulkiness does not increase around the reaction point in the present invention, because 5-halo-1-pentyne (5) is used as the starting material, which is free of an oxygen atom which is prone to interact with copper or magnesium. According to the present invention, use is made of a copper catalyst which is converted into an organocopper reagent having a proper nucleophilicity. As a result, it becomes possible to selectively promote the $S_N2$ reaction at the propargyl position. It is therefore possible to produce 10-halo-3,6-decadiyne (1) with a high yield.

The reaction temperature of the coupling is preferably in a range of from 50 to 80° C. in view of the reaction rate.

The duration of the coupling step may vary depending on a scale of a reaction system. It ranges preferably from 1 to 50 hours in view of the yield.

Examples of $X^1$ in the 10-halo-3,6-decadiyne of the general formula (1) are as mentioned above.

Non-limiting examples of the 10-halo-3,6-decadiyne (1) include 10-chloro-3,6-decadiyne, 10-bromo-3,6-decadiyne, and 10-iodo-3,6-decadiyne, with 10-chloro-3,6-decadiyne being preferable in view of the stability.

Next, a process for preparing a (3Z,6Z)-10-halo-3,6-decadiene (2) will be described in more detail.

A (3Z,6Z)-10-halo-3,6-decadiene (2) may be prepared by reducing the 10-halo-3,6-decadiyne (1).

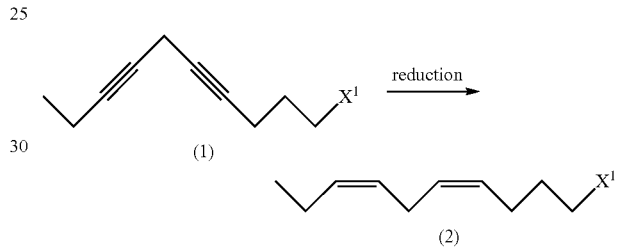

The reduction may be a catalytic hydrogenation; a reduction with zinc in an alcohol solvent; a reduction by hydroboration with a dialkylborane, followed by protonation; a reduction with potassium hydroxide and N,N-dimethylformamide (DMF) in the presence of a palladium catalyst such as palladium acetate; and a reduction by hydrosilylation to form a vinylsilane, followed by desilylation. In view of the selectivity and productivity, a catalytic hydrogenation, a reduction with zinc in an alcohol solvent, and a reduction by hydroboration with a dialkylborane, followed by protonation are preferable, with a catalytic hydrogenation being more preferable.

The catalytic hydrogenation may be carried out by introducing a hydrogen gas in the presence of a metal catalyst.

Non-limiting examples of the metal catalyst that may be used in the catalytic hydrogenation include Lindlar catalyst; nickel catalysts, such as P-2 nicekl boride catalyst (Thomas J. Caggiano et al. Encyclopedia of Reagents for Organic Synthesis: 3694-3699) (hereinafter also called "P-2Ni catalyst"); and palladium catalysts, such as a palladium-carbon catalyst, and a Pd-PEI catalyst which comprises palladium-carbon poisoned with a polyethyleneimine polymer (PEI). In view of the economical efficiency, the Lindlar catalyst and nickel catalysts are preferable.

The amount of the metal catalyst may be different among catalysts. In a case where the catalyst is solid, such as the Lindlar catalyst, it is used preferably in an amount of from 0.01 to 50 grams per mole of the 10-halo-3,6-decadiyne (1) in view of the reactivity. In a case of a P-2Ni catalyst, it is preferably used so that the amount of the corresponding nickel compound ranges from 0.001-0.50 mole per mole of the 10-halo-3,6-decadiyne (1).

It should be noted that a solid catalyst may be dispersed in a solvent.

When the activity of the metal catalyst is too high, a catalyst poison may be used as needed.

Non-limiting examples of the catalyst poison that may be used in the catalytic hydrogenation include amine compounds, such as pyridine, quinoline, and ethylenediamin; and sulfur compounds, such as benzenethiol, diphenyl sulfide, dimethyl sulfide, and dimethyl sulfoxide.

The amount of the catalyst poison may be different among catalyst poisons. It ranges preferably from 0.0001 to 10.0 grams per mole of the 10-halo-3,6-decadiyne (1) in view of the reaction rate and the geometric selectivity.

Non-limiting examples of the solvent that may be used in the catalytic hydrogenation include polar solvents, such as acetonitrile, ethyl acetate, and methyl acetate; hydrocarbon solvents, such as toluene, pentane, hexane, heptane, cyclohexane, and cyclohexene; and alcohol solvents, such as methanol, ethanol, propanol, butanol, pentanol, hexanol, 2-propanol, 2-butanol, and cyclohexanol. These solvents may be used alone or in combination.

When the Lindlar catalyst is used, a hydrocarbon solvent such as hexane is preferable in view of the reactivity. When a nickel catalyst is used, an alcohol solvent, such as methanol, ethanol, propanol, butanol and 2-propanol, is preferable in view of the reactivity. When a palladium catalyst, such as palladium carbon, is used, a polar solvent, such as methyl acetate and ethyl acetate, is preferable in view of the reactivity.

The amount of the solvent to be used may vary depending on the types of catalyst and solvent. It ranges preferably from 0 to 1,000 grams per mole of the 10-halo-3,6-decadiyne (1) in view of the reactivity.

The temperature in the catalytic hydrogenation may vary depending on the types of catalyst and solvent to be used. It ranges preferably from 40 to 160° C. in view of the geometrical selectivity.

The duration of the catalytic hydrogenation step ranges preferably from 1 to 50 hours in view of the yield.

The reduction may be carried out with zinc in an alcohol solvent.

Alcohols that may be used as the solvent preferably have 1 to 10 carbon atoms, more preferably 1 to 5 carbon atoms. Non-limiting examples of alcohols for use as the solvent include linear alcohols, such as methanol, ethanol, propanol, butanol, pentanol, hexanol, heptanol, octanol, nonanol, and decanol; branched alcohols, such as 2-propanol and 2-butanol; and cyclic alcohols such as cyclohexanol. In view of the reactivity, alcohols having 1 to 5 carbon atoms, such as methanol, ethanol, propanol, butanol, pentanol, and 2-propanol, are preferable. The amount of the alcohol to be used ranges preferably from 46 to 1,000 grams per mole of the 10-halo-3,6-decadiyne (1) in view of the reactivity.

As used herein, the term "zinc" is intended to mean metal zinc or activated zinc as hereinafter described in more detail. The amount of zinc to be used ranges preferably from 1.0 to 20.0 moles per mole of the 10-halo-3,6-decadiyne (1), in view of the reactivity.

The reduction with zinc in an alcohol solvent may require a prolonged reaction time due to low reactivity of zinc. If necessary, an activating agent for the activation of zinc may be added, or activated zinc prepared in advance may be used.

Non-limiting examples of the activating agent include 1,2-dibromoethane, cuprous chloride, cuprous bromide, cuprous iodide, lithium bromide, iodine, and chlorotrimethylsilane. These activating agents may be used alone or in combination. The amount of the activating agent to be used ranges preferably from 0.01 to 10.0 moles per mole of the 10-halo-3,6-decadiyne (1), in view of the reactivity.

The activated zinc may be prepared, e.g., by treating metal zinc with an acid such as hydrochloric acid, or by reducing zinc chloride with metal lithium in tetrahydrofuran.

The temperature in the reduction with zinc in an alcohol solvent may vary depending on the type of solvent to be used. It ranges preferably from 20 to 120° C. in view of the reactivity.

The duration of the reduction with zinc in an alcohol solvent ranges preferably from 1 to 150 hours for completion of the reaction.

In the reduction by hydroboration with a dialkylborane, followed by protonation, the hydroboration is carried out using a dialkylborane in a solvent. Dialkylboranes that may be used for the hydroboration preferably have 4 to 12 carbon atoms, more preferably 6 to 12 carbon atoms. Non-limiting examples of the dialkylborane include dicyclohexylborane, diisoamylborane, disiamylborane, 9-borabicyclo[3.3.1]nonane (9-BBN), diisopinocampheylborane, catecholborane, and pinacolborane, with dicyclohexylborane and diisoamylborane being preferable in view of the reactivity. The amount of the dialkylborane to be used ranges preferably from 2.0 to 4.0 moles per mole of the 10-halo-3,6-decadiyne (1), in view of the reactivity.

Non-limiting examples of the solvent that may be used for the hydroboration include hydrocarbon solvents, such as toluene, xylene, hexane, and cyclohexane; and ether solvents, such as tetrahydrofuran, 4-methyltetrahydropyran, diethyl ether, and diethyleneglycol dimethyl ether, with tetrahydrofuran and diethyleneglycol dimethyl ether being preferable in view of the reactivity. These solvents may be used alone or in combination. The amount of the solvent to be used ranges preferably from 100 to 3,000 grams per mole of the 10-halo-3,6-decadiyne (1), in view of the reactivity.

The reaction temperature of the hydroboration is preferably in a range of from −20° C. to 30° C. in view of the geometric selectivity. The duration of the hydroboration step may vary depending on a reaction temperature or a scale of a reaction system. It ranges preferably from 1 to 20 hours in view of the yield.

The protonation subsequent to the hydroboration may be carried out using an acid in a solvent.

Non-limiting examples of the acid that may be used in the protonation subsequent to the hydroboration include carboxylic acids, such as acetic acid, propionic acid, butyric acid, pentanoic acid, pivalic acid, heptanoic acid, trifluoroacetic acid, chloroacetic acid, formic acid, and oxalic acid; sulfonic acids, such as p-toluene sulfonic acid; and mineral acids, such as sulfuric acid, hydrochloric acid, nitric acid, and phosphoric acid, with carboxylic acids such as acetic acid and propionic acid being preferable in view of the reactivity. The amount of the acid to be used ranges preferably from 2.0 to 20.0 moles per mole of the 10-halo-3,6-decadiyne (1), in view of the reactivity.

Because the protonation is carried out in situ after the hydroboration, types and amounts of the solvent to be used for the protonation do not change.

The temperature in the protonation may vary depending on the type of reagent to be used. It ranges preferably from 0° C. to 150° C. in view of the reaction rate. The duration of the protonation step may vary depending on the reaction temperature or a scale of a reaction system. It ranges preferably from 1 to 20 hours in view of the reactivity.

The reduction with potassium hydroxide and N,N-dimethylformamide (DMF) in the presence of a palladium catalyst such as palladium acetate may be carried out at a temperature in the range of from 100° C. to 180° C. for a period of from 6 to 100 hours.

In the reduction by hydrosilylation to form a vinylsilane, followed by desilylation, the hydrosilylation may be carried out using a trialkylsilane and a metal catalyst, such as Wilkinson catalyst or Trost catalyst.

The hydrosilylation is preferably carried out at a temperature of 5° C. to 100° C. for a period of 1 to 20 hours.

The desilylation after the hydrosilylation is preferably carried out using an acid, such as hydrogen iodide, acetyl chloride, sulfuric acid, and hydrochloric acid, or titanium tetrachloride or iodine at a temperature of 5° C. to 80° C. for a period of 1 to 20 hours.

Non-limiting examples of $X^1$ in the general formula (2) for the (3Z,6Z)-10-halo-3,6-decadiene are as described above.

Non-limiting examples of (3Z,6Z)-10-halo-3,6-decadiene (2) include (3Z,6Z)-10-chloro-3,6-decadiene, (3Z,6Z)-10-bromo-3,6-decadiene, and (3Z,6Z)-10-iodo-3,6-decadiene, with (3Z,6Z)-10-chloro-3,6-decadiene being preferable in view of the stability.

Next, a process for preparing (4Z,7Z)-4,7-decadien-1-yl acetate (4) will be described in more detail.

The desired compound, (4Z,7Z)-4,7-decadien-1-yl acetate (4), may be prepared by directly converting the halogen atom in the (3Z,6Z)-10-halo-3,6-decadiene (2) into an acetoxy group, or by converting the halogen atom into another substituent such as a hydroxyl group and then converting it into an acetoxy group.

Non-limiting examples of the process for converting the halogen atom into an acetoxy group include a process of acetoxylating the (3Z,6Z)-10-halo-3,6-decadiene (2) with an acetate salt; a process of reacting the (3Z,6Z)-10-halo-3,6-decadiene (2) with an alkali metal hydroxide to form (3Z, 6Z)-3,6-decadien-10-ol, followed by acetylation; and a process of reacting the (3Z,6Z)-10-halo-3,6-decadiene (2) with a metal alkoxide, followed by an ether cleavage reaction with a strong acid to form (3Z,6Z)-3,6-decadien-10-ol, followed by acetylation. In view of the number of process steps, a process of acetoxylating the (3Z,6Z)-10-halo-3,6-decadiene (2) with an acetate salt is preferable.

First, a process of acetoxylating a (3Z,6Z)-10-halo-3,6-decadiene (2) with an acetate salt of the general formula (3) will be described in more detail.

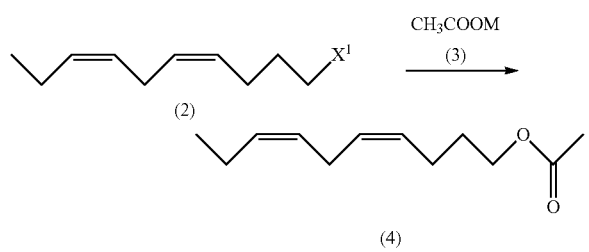

In the acetate salt (3), M is a metal atom, including alkali metals, such as lithium, sodium, and potassium.

Non-limiting examples of the acetate salt (3) include lithium acetate, sodium acetate, and potassium acetate, with sodium acetate being preferable in view of the reactivity.

The amount of the acetate salt (3) to be used for the acetoxylation ranges preferably from 1.0 to 2.0 moles per mole of the (3Z,6Z)-10-halo-3,6-decadiene (2), in view of the reactivity.

A solvent may be used in the acetoxylation reaction. Examples of the solvent includes hydrocarbon solvents, such as toluene, xylene, and hexane; ether solvents, such as tetrahydrofuran, 4-methyltetrahydropyran, and diethyl ether; and polar solvents, such as N,N-dimethylformamide, N,N-dimethylacetamide, acetonitrile, and dimethyl sulfoxide. In view of the reactivity, polar solvents such as N,N-dimethylformamide are preferable. These solvents may be used alone or in combination. The amount of the solvent to be used ranges preferably from 20 to 2,000 grams per mole of the (3Z,6Z)-10-halo-3,6-decadiene (2) in view of the reactivity.

The temperature in the acetoxylation may vary depending on the type of solvent to be used. It ranges preferably from 64 to 189° C. in view of the reaction rate. The duration of the acetoxylation step may vary depending on the type of solvent to be used or a scale of a reaction system. It ranges preferably from 1 to 35 hours in view of the yield.

The desired compound, (4Z,7Z)-4,7-decadien-1-yl acetate (4), may also be prepared by a process of reacting the (3Z,6Z)-10-halo-3,6-decadiene (2) with an alkali metal hydroxide to form (3Z,6Z)-3,6-decadien-10-ol, followed by acetylation. Non-limiting examples of the alkali metal hydroxide include lithium hydroxide, sodium hydroxide, and potassium hydroxide. The acetylation can be conducted in any conventional manner.

The desired compound, (4Z,7Z)-4,7-decadien-1-yl acetate (4), may also be prepared by a process of reacting the (3Z,6Z)-10-halo-3,6-decadiene (2) with a metal alkoxide, followed by an ether cleavage reaction with a strong acid to form (3Z,6Z)-3,6-decadien-10-ol, followed by acetylation. Non-limiting examples of the metal alkoxide include sodium tert-butoxide and potassium tert-butoxide. The ether cleavage reaction with a strong acid and the acetylation can be conducted in any conventional manner.

In the manner described above, (4Z,7Z)-4,7-decadien-1-yl acetate (4), sex pheromone of the lesser date moth which is an insect pest serious for date palm, can be prepared.

EXAMPLES

The present invention will be further illustrated by the following Examples, which should not to be construed to limit the scope of the invention.

Example 1: Production of 10-chloro-3,6-decadiyne (1A), i.e., $X^1$ is Cl

Methyl magnesium chloride (352.38 g, 4.73 moles) and tetrahydrofuran (1476 g) were charged to a reactor, and stirred at 50-60° C. for 20 minutes. Then, 5-chloro-1-pentyne (461.52 g, 4.50 moles) was added dropwise at 50-65° C., followed by aging at 60-65° C. for 3 hours. After the aging, cuprous chloride (4.46 g, 0.045 mole) was added while keeping the internal temperature at 55-60° C., followed by the dropwise addition of 1-bromo-2-pentyne (628.47 g, 4.28 moles) at 50-60° C. After completion of the dropwise addition, the reaction mixture was aged at 60-65° C. for 2 hours. After cooling to 30° C., the reaction was stopped by the addition of 3.1 wt. % hydrochloric acid (1,927 g). The organic layer was washed with 12 wt. % hydrochloric acid and a 4 wt. % aqueous ammonia solution. After condensation under reduced pressure, the resulting residue was distilled under reduced pressure to obtain 10-chloro-3,6-decadiyne (1A) (bp: 96.9-97.7° C. [3 mmHg], 662.67 g, 3.93 moles) with a yield of 91.9%.

Characterization of 10-chloro-3,6-decadiyne (1A)

[NMR Spectra] $^1$H-NMR (500 MHZ, CDCl$_3$): δ1.11 (3H, t, J=7.3 HZ), 1.93 (2H, quint-like, J=6.5 HZ), 2.16 (2H, qt, J=7.3, 2.3 HZ), 2.34 (2H, tt, J=6.9 HZ), 3.10 (2H, quint-like, J=2.3 HZ), 3.63 (2H, t-like, J=6.5 HZ); $^{13}$C-NMR (125 MHZ, CDCl$_3$): δ9.62, 12.33, 13.82, 16.15, 31.39, 43.69, 73.48, 75.66, 78.34, 81.93.

[Mass Spectra] EI-Mass Spectrum (70 eV): m/Z 167 (M$^+$–1), 153, 140, 115, 105, 91, 77, 41.

[IR Absorption Spectra] (NaCl): νmax 2976, 2938, 2918, 1435, 1321, 1290, 727, 654.

Example 2: Production of 10-chloro-3,6-decadiyne (1A)

Methyl magnesium chloride (52.35 g, 0.70 mole) and tetrahydrofuran (218.55 g) were charged to a reactor, and stirred at 50-60° C. for 20 minutes. Then, 5-chloro-1-pentyne (71.79 g, 0.70 mole) was added dropwise at 50-65° C., followed by aging at 60-65° C. for 3 hours. After the aging, cuprous chloride (0.693 g, 0.007 mole) was added while keeping the internal temperature at 55-60° C., followed by the dropwise addition of 1-bromo-2-pentyne (102.91 g, 0.70 mole) at 50-60° C. After completion of the dropwise addition, the reaction mixture was aged at 60-65° C. for 2 hours. After cooling to 30° C., the reaction was stopped by the addition of 3.1 wt. % hydrochloric acid (299.81 g). The organic layer was washed with 12 wt. % hydrochloric acid and a 4 wt. % aqueous ammonia solution. After condensation under reduced pressure, the resulting residue was distilled under reduced pressure to obtain 10-chloro-3,6-decadiyne (1A) (bp: 96.9-97.7° C. [3 mmHg], 109.49 g, 0.65 mole) with a yield of 92.7%.

Example 3: Production of (3Z,6Z)-10-chloro-3,6-decadiene (2A), i.e., X$^1$ is Cl To a reactor were charged 10-chloro-3,6-decadiyne (145.92 g, 0.87 mole), Lindlar catalyst (0.91 g), quinoline (0.31 g, 0.0024 mole), and hexane (145.92 g). After elevating the temperature to 45-55° C., a hydrogen gas was introduced. After completion of the reaction, the reactor chamber was purged with a nitrogen gas, and water (75 g) was added for washing. After separation of the aqueous layer, the organic layer was condensed under reduced pressure, and the resulting residue was distilled under reduced pressure to obtain (3Z,6Z)-10-chloro-3,6-decadiene (2A) (bp: 78.9° C. [3 mmHg], 128.33 g, 0.74 mole) with a yield of 85.9%.

Characterization of (3Z,6Z)-10-chloro-3,6-decadiene (2A)

[NMR Spectra] $^1$H-NMR (500 MHZ, CDCl$_3$): δ0.98 (3H, t, J=7.6), 1.84 (2H, quint-like, J=7.1), 2.08 (2H, quint-like, J=7.2), 2.23 (2H, q-like, J=7.3), 2.80 (2H, br.t, J=6.9), 3.54 (2H, t, J=6.9), 5.27-5.46 (4H, m); $^{13}$C-NMR (125 MHZ, CDCl$_3$): δ14.24, 20.52, 24.33, 25.50, 32.33, 44.43, 126.96, 127.80, 129.76, 132.02.

[Mass Spectra] EI-Mass Spectrum (70 eV): m/Z 172 (M$^+$), 157, 143, 130, 95, 81, 67, 55, 41.

[IR Absorption Spectra] (NaCl): νmax 3010, 2962, 2934, 2873, 1455, 1444, 726, 654.

Example 4: Production of (4Z,7Z)-4,7-decadien-1-yl acetate (4)

To a reactor were charged (3Z,6Z)-10-chloro-3,6-decadiene (127.70 g, 0.74 mole), sodium acetate (84.89 g, 1.04 moles) and N,N-dimethylacetamide (97.61 g), and the resulting mixture was stirred at 120-140° C. for 8 hours. Then, after the reaction mixture was cooled to 60° C., water (333 g) was added, and the resulting reaction mixture was separated. The organic layer was further 16 washed with water, and the separated organic layer was condensed under reduced pressure, and the resulting residue was distilled under reduced pressure to obtain (4Z,7Z)-4,7-decadien-1-yl acetate (4) (bp: 98.2-103.2° C. [3 mmHg], 130.24 g, 0.66 mole) with a yield of 89.7%.

Characterization of (4Z,7Z)-4,7-decadien-1-yl acetate (4)

[NMR Spectra] $^1$H-NMR (500 MHZ, CDCl$_3$): δ0.96 (3H, t, J=7.6), 1.68 (2H, quint-like, J=6.9), 2.03 (3H, s), 2.06 (2H, quint-like, J=7.2), 2.13 (2H, q-like, J=7.1), 2.76 (2H, br.t, J=6.9), 4.05 (2H, t, J=6.9), 5.24-5.42 (4H, m); $^{13}$C-NMR (125 MHZ, CDCl$_3$): δ14.20, 20.48, 20.91, 23.49, 25.40, 28.42, 63.88, 126.98, 128.36, 129.18, 131.91, 171.08.

[Mass Spectra] EI-Mass Spectrum (70 eV): m/Z 196 (M$^+$), 153, 136, 121, 107, 93, 79, 67, 55, 43.

[IR Absorption Spectra] (NaCl): νmax 3011, 2963, 2935, 1743, 1366, 1240, 1042, 720.

The invention claimed is:

1. A process for preparing (4Z,7Z)-4,7-decadien-1-yl acetate, comprising at least the following steps:

reducing a 10-halo-3,6-decadiyne of the general formula (1):

(1)

wherein X$^1$ is a halogen atom, to form a (3Z,6Z)-10-halo-3,6-decadiene of the general formula (2):

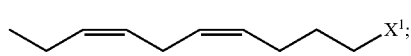

(2)

and converting the (3Z,6Z)-10-halo-3,6-decadiene into (4Z, 7Z)-4,7-decadien-1-yl acetate of the formula (4) having an acetoxy group in place of the halogen atom of the (3Z,6Z)-10-halo-3,6-decadiene:

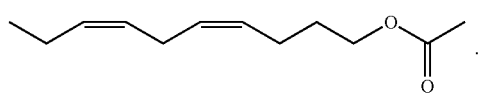

(4)

2. The process for preparing (4Z,7Z)-4,7-decadien-1-yl acetate according to claim 1, said process further comprising the steps of:

deprotonating a 5-halo-1-pentyne of the general formula (5):

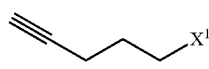

(5)

by a reaction with a Grignard reagent of the general formula (6):

RMgX$^2$ (6)

wherein R is a monovalent hydrocarbon group having 1-18 carbon atoms, and X$^2$ is a halogen atom,
to form a 5-halo-1-pentynyl magnesium halide of the general formula (7):

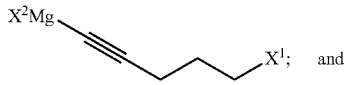 (7)

coupling the 5-halo-1-pentynyl magnesium halide, in the presence of a copper catalyst, with a 1-halo-2-pentyne of the general formula (8):

 (8)

wherein X$^3$ is a halogen atom,
to form the 10-halo-3,6-decadiyne of the general formula (1).

3. The process for preparing (4Z,7Z)-4,7-decadien-1-yl acetate according to claim 1, wherein said reducing step includes a catalytic hydrogenation, a reduction with zinc in an alcohol solvent, or a reduction by hydroboration with a dialkylborane, followed by protonation.

4. A process for preparing a 10-halo-3,6-decadiyne of the general formula (1):

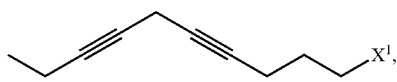 (1)

wherein X$^1$ is a halogen atom, said process comprising the steps of:
deprotonating a 5-halo-1-pentyne of the general formula (5):

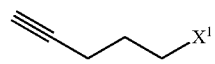 (5)

by a reaction with a Grignard reagent of the general formula (6):

RMgX$^2$ (6)

wherein R is a monovalent hydrocarbon group having 1-18 carbon atoms, and X$^2$ is a halogen atom,
to yield a 5-halo-1-pentynyl magnesium halide of the general formula (7):

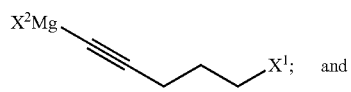 (7)

coupling the 5-halo-1-pentynyl magnesium halide, in the presence of a copper catalyst, with a 1-halo-2-pentyne of the general formula (8):

 (8)

wherein X$^3$ is a halogen atom,
to form the 10-halo-3,6-decadiyne.

5. The process for preparing (4Z,7Z)-4,7-decadien-1-yl acetate according to claim 2, wherein said reducing step includes a catalytic hydrogenation, a reduction with zinc in an alcohol solvent, or a reduction by hydroboration with a dialkylborane, followed by protonation.

* * * * *